United States Patent
Sauvageau

(10) Patent No.: US 7,351,222 B2
(45) Date of Patent: Apr. 1, 2008

(54) DRAINAGE CATHETER WITH VISUAL INDICATOR AND/OR LOCK SYSTEM

(75) Inventor: David J. Sauvageau, Methuen, MA (US)

(73) Assignee: Scimed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 11/635,702

(22) Filed: Dec. 7, 2006

(65) Prior Publication Data

US 2007/0083154 A1 Apr. 12, 2007

Related U.S. Application Data

(62) Division of application No. 10/104,597, filed on Mar. 22, 2002, now Pat. No. 7,192,415.

(51) Int. Cl.
*A61M 3/00* (2006.01)

(52) U.S. Cl. .................................. 604/95.04

(58) Field of Classification Search ............ 604/95.04, 604/95.01; 600/144, 145, 146, 147, 148, 600/149
See application file for complete search history.

(56) References Cited

U.S. PATENT DOCUMENTS

| | | | |
|---|---|---|---|
| 3,876,234 A | 4/1975 | Harms | |
| 4,643,720 A | 2/1987 | Lanciano | |
| 4,740,195 A | 4/1988 | Lanciano | |
| 4,895,570 A | 1/1990 | Larkin | |
| 5,041,085 A | 8/1991 | Osborne et al. | |
| 5,185,004 A | 2/1993 | Lashinski | |
| RE34,223 E | 4/1993 | Bonaldo | |
| 5,352,198 A | 10/1994 | Goldenberg et al. | |
| 5,399,165 A | 3/1995 | Paul, Jr. | |
| 5,419,764 A | 5/1995 | Roll | |
| 5,465,716 A | 11/1995 | Avitall | |
| 5,522,400 A | 6/1996 | Williams | |
| 5,598,840 A | 2/1997 | Iund et al. | |

(Continued)

FOREIGN PATENT DOCUMENTS

EP 1 046 406 A2 10/2000
WO WO 98/33429 8/1998

OTHER PUBLICATIONS

Invitation to Pay Additional Fees w/Annex "Communication Pertaining to the Results of the Partial International Search" in corresponding International Appl. PCT/US03/07758, dated Sep. 10, 2003.

*Primary Examiner*—Sharon E. Kennedy
(74) *Attorney, Agent, or Firm*—RatnerPrestia

(57) ABSTRACT

A catheter comprising a tube having a distal end for deployment in a patient, and a proximal end for remaining outside of the patient; an anchoring mechanism at the distal end of the tube having a fully open configuration, a fully closed configuration, and a range of configurations therebetween; a filamentary member attached to the anchoring mechanism for controlling the configuration of the anchoring mechanism; and a controller located at or near the proximal end of the tube for controlling the filamentary member, wherein the controller comprises an indicator for visually indicating the anchoring mechanism configuration, a locking mechanism for locking the anchoring mechanism in the fully closed configuration; or a combination of the visual indicator and the locking mechanism.

25 Claims, 6 Drawing Sheets

U.S. PATENT DOCUMENTS

| | | |
|---|---|---|
| 5,611,777 A | 3/1997 | Bowden et al. |
| 5,674,203 A | 10/1997 | Lewandowski |
| 5,935,141 A | 8/1999 | Weldon |
| 5,937,885 A | 8/1999 | Sampson |
| 5,941,849 A | 8/1999 | Amos, Jr. et al. |
| 6,042,577 A | 3/2000 | Chu et al. |
| 6,159,177 A | 12/2000 | Amos, Jr. et al. |
| 6,183,435 B1 | 2/2001 | Bumbalough et al. |
| 6,206,897 B1 | 3/2001 | Jamiolkowski et al. |
| 6,224,587 B1 | 5/2001 | Gibson |
| 6,231,542 B1 | 5/2001 | Amos, Jr. et al. |
| 6,508,789 B1 | 1/2003 | Sinnott et al. |
| 6,955,673 B2 | 10/2005 | Lentz |
| 2003/0125663 A1 | 7/2003 | Coleman et al. |
| 2004/0039338 A1 | 2/2004 | Lee et al. |

DRAINAGE CATHETER WITH VISUAL INDICATOR AND/OR LOCK SYSTEM

CROSS REFERENCE TO RELATED APPLICATION

This application is a Divisional of U.S. application Ser. No. 10/104,597, filed Mar. 22, 2002 now U.S. Pat. No. 7,192,415.

TECHNICAL FIELD

This invention relates generally to catheters and, more specifically, to drainage catheters having means for retaining the distal end of the catheter in a predetermined configuration.

BACKGROUND OF THE INVENTION

There are a variety of therapies or treatment modalities that require a catheter with a distal anchor or the like to retain the catheter in position. One particular application involves catheters used for drainage purposes. Generally, these catheters are introduced into a patient through a large hypodermic needle or trocar. A guidewire is inserted through the needle or trocar which is then removed. The catheter tube, with a stiffening cannula, passes over the guidewire into the cavity. The cannula and guidewire can then be withdrawn leaving a portion of the catheter at its distal end in the desired cavity.

Various catheters have been developed with diverse anchor structures to prevent inadvertent removal of the catheter. Referring now to FIG. 1, one such anchor comprises a "pigtail loop" configuration 100 (shown in dashed lines) of distal flexible tube portion 102 at or near the distal end of catheter 104. The pigtail loop configuration 100 of portion 102 is also referred to herein as a "closed" configuration. Portion 102 also has an open configuration 101, shown in solid lines in FIG. 1, in which the portion is straight rather than curved. Portion 102 has a number of ports 106 to ensure drainage. The pigtail loop configuration 100 prevents accidental removal of the catheter from the patient. Generally pigtail loop 100 is preformed in the catheter because the flexible tube of the catheter is formed of a memory material. For introduction into a patient, a stiff cannula (not shown) or similar implement is inserted through the catheter lumen 108 to straighten the pigtail loop. The distal end of the flexible tube returns to the pigtail loop configuration after the cannula is removed. Typically a suture thread 110, thin cable, or other filamentary member extends through draw ports 106a and 106b at two spaced positions along the distal portion of the flexible tube. The term "suture" as used herein throughout for simplicity to refer to the filamentary member does not imply any limitation to the type of filamentary member. These ports come into juxtaposition when the pigtail loop 100 forms after the physician removes the cannula. Then the physician will take up any slack in suture 110 that leads proximally from pigtail loop 100. When suture 110 is made taut, it holds the juxtaposed ports 106a and 106b of the catheter together and thereby prevents the pigtail loop from straightening. If only a portion of suture 110 is drawn proximally, the suture will still prevent the pigtail loop from straightening completely.

When it is appropriate to remove the catheter, a stiff cannula is inserted through the lumen 108 with suture 110 still taut until the cannula reaches pigtail loop 100. The tension in suture 110 minimizes the chances for the cannula entangling with the filamentary member. Thereafter the tension on suture 110 is released before or while the stiff cannula is advanced distally to straighten the pigtail loop and facilitate the removal of the catheter from the patient.

A number of structures or "controllers" are known in the art for taking up the slack in suture 110, some of which are twist-locking designs by which axial rotation of a barrel at the end of the catheter causes tightening of the filamentary member. U.S. Pat. No. 5,419,764 to Roll and U.S. Pat. No. 6,042,577 to Chu et al., both incorporated herein by reference, disclose exemplary structures incorporating twist locks. U.S. Pat. No. 5,941,849 and a continuation thereof, U.S. Pat. No. 6,231,542, by Amos, Jr. et al., both of which are assigned to the assignee of the present invention and incorporated herein by reference, disclose several other controller designs.

More details of an exemplary controller 10 are shown in FIGS. 2A-2C. Controller 10 comprises a spindle 12 that fits radially over catheter 11, strain relief 13, end cap 14 having a notch 15 to allow it to snap onto the spindle, threaded washer 16 that is split for installation over the spindle, O-ring 17 that fits in a channel defined by proximal shoulder 18a and distal shoulder 18b, winding washer 19, and hub 20. Internal threads in hub 20 (not shown) allow hub to be twisted on threaded washer 16, the eight flanges 21 on winding washer 19 interlocking with the octagonal periphery of hub 20 to rotate the winding washer in concert with the hub. Hub 20 comprises an integral luer connection 24. Suture 110 is threaded through port 25 communicating between an inner lumen 109 in spindle 12 and the outer surface 26 of the proximal end 27 of spindle 12. The proximal end of suture 110 is attached to the winding washer through holes 23. Thus, twisting hub 20 about spindle 12 on threaded washer 16 twists the winding washer by engagement of the polygonal inner periphery of the hub with the outer periphery of the washer, to helically wind the suture about the outer surface 26 of spindle proximal end 27, taking up the slack in the suture.

Threaded washer 16 is mounted on a flattened portion 22 of spindle 12 having a non-round cross-section, as shown in FIG. 2C, but is free to move axially when hub 20 is rotated. Thus, rotation of hub 20 does not cause the hub to move axially, but rather moves threaded washer 16 axially, as described in more detail in the '849 and '542 patents. End cap 14 and distal shoulder 18b of the channel for O-ring 17 create the proximal and distal axial boundaries respectively for movement of threaded washer 16.

The '849 and '542 patents further disclose embodiments wherein the pitch of the threads on washer 16 is chosen so that the fully closed pigtail configuration of 100 and fully open configuration 101 coincide with the threaded washer abutting the corresponding axial boundaries. In practice, however, it has proven preferable for the axial boundary of travel for washer 16 at end cap 14 not to coincide with the fully closed pigtail configuration 100. In part, this is because it is preferred for a single controller design to be used with different pigtail sizes, which would require different threaded washers and mating hubs to be provided in the controller for each size pigtail.

Thus, controller 10 shown in FIGS. 2A-2C lacks means for indicating to the practitioner when the pigtail is fully closed. Consequently, practitioners tend to stop twisting based on the amount of resistance that they feel. This may lead to undertwisting or overtwisting, both of which may have adverse consequences. Undertwisting may result in the pigtail not being fully closed, which, if the catheter is not firmly anchored, may cause the catheter to become dislodged and fall out. Overtwisting may stress the filamentary member to the point that it snaps, requires removal of the catheter and replacement with a new one. Thus, there is a need in the art for drainage catheters that can indicate closure of the anchor mechanism.

Strain relief 13 as shown in FIGS. 1-2B comprises a flexible, releasable tubular section 28 shown in rolled configuration 29A in FIG. 2A and in dashed lines in FIG. 2B, and in a fully extended configuration 29B (solid lines) in FIG. 1 and FIG. 2B. When tubular section 28 is unrolled in the fully extended configuration 29B, it prevents rotation of hub 20 relative to spindle 12 because of the frictional resistance to rotation of strain relief 13 on spindle 12. Although this may prevent a patient from unintentionally twisting hub 20 and loosening suture 110, which would have the effect of undoing pigtail 100, controller 10 shown in FIGS. 1-2C lacks any means to prevent patients from intentionally doing so. Thus, a motivated patient may merely unroll portion 28 and then freely twist hub 20. Furthermore, the frictional resistance between strain relief 13 and spindle 12 may be overcome with sufficient force. Thus, there is also a need in the art for drainage catheters that can prevent intentional and/or unintentional unlocking of the catheter when in the closed configuration.

SUMMARY OF THE INVENTION

One aspect of the invention comprises a catheter having an anchoring mechanism, such as but not limited to a pigtail, at the distal end of the tube with a filamentary member attached to the anchoring mechanism for controlling its configuration, and a controller located at or near the proximal end of the tube for controlling the filamentary member, in which the controller comprises an indicator for visually indicating the anchoring mechanism configuration. In one embodiment, the controller comprises a first member, such as a hub, coaxial with the tube and rotatable about the tube axis, and the visual indicator comprises a window in the first member through which a second member, such as an axially movable threaded washer, is visible when the anchoring mechanism is in a particular configuration, such as the fully closed configuration.

Another aspect of the invention comprises a locking mechanism for locking the anchoring mechanism in the fully closed configuration. In one embodiment, the locking mechanism comprises slide that is not rotatable on the tube axis relative to the tube, but is movable axially relative to the tube between a proximal position and a distal position. A substantially flat radially inward surface of the slide is radially spaced a first radial distance from the tube axis, and the hub comprises a flattened region adapted to be engaged by the substantially flat surface of the slide when the slide is in the proximal position. The substantially flat surface may have a first surface formation, such as a protrusion, adapted to interlock with a second surface formation, such as an indentation, in the hub for preventing axial movement of the slide when the two surface formations are interlocked. The slide may further comprise a specialized tool means for unlocking the interlocked first surface formation and second surface formation.

Embodiments comprising the visual indicator alone, the locking mechanism alone, or a combination of both are within the scope of this invention. One catheter embodiment may comprise the tube, the anchoring mechanism, the filamentary member for controlling the anchoring mechanism, and the controller for controlling the filamentary member. The controller may comprise a spindle coaxially mounted on the tube and having a proximal reel portion comprising an outer surface having the winding diameter, a second lumen extending proximally from the first lumen, and a radial port connecting the outer surface with the second lumen. A hub coaxial with the tube and the spindle is rotatable about the axis and has internal threads and a window therein. An axially translatable threaded washer coaxial with the spindle and not rotatable relative to the spindle, has external threads for mating with the internal threads of the hub. A winding washer attached to a proximal end of the filamentary member is rotatable about the spindle. The filamentary member extends through the first lumen into the second lumen and out through the radial port to the winding washer. Twisting the hub about the axis rotates the winding washer and helically winds the filamentary member about the reel portion outer surface while also axially translating the threaded washer. Visibility of the threaded washer within the hub window indicates when the anchoring mechanism is in the closed configuration.

In one embodiment of the controller, the hub comprises a substantially flat region and the controller further comprises a slide that is not rotatable about the tube axis relative to the tube, but is movable axially relative to the tube between a proximal position and a distal position. The slide has a substantially flat radially inward surface that is radially spaced a first radial distance from the axis and adapted to engage the substantially flat region of the hub when the slide is in the proximal position to lock the hub in a fixed rotational position.

Yet another aspect of the invention comprises a method for deploying a drainage catheter having a visual indicator and/or locking mechanism as described herein. Such a method comprises inserting the drainage catheter into a patient with the anchoring mechanism in the fully open configuration; and manipulating the controller until the indicator indicates that the anchoring mechanism is in the fully closed configuration. Where the catheter comprises a locking mechanism, the method comprises engaging the locking mechanism to lock the anchoring mechanism in the fully closed configuration. Where the locking mechanism further comprises means a specialized tool for unlocking the mechanism, the method further comprising unlocking the locking mechanism using the specialized tool; manipulating the anchoring mechanism into the open configuration; and removing the drainage catheter from the patient.

Another aspect of the invention comprises an improvement to a catheter comprising (a) a tube having an axis, a distal end for deployment in a patient, and a proximal end for remaining outside of the patient; (b) an anchoring mechanism at the distal end of the tube having a fully open configuration, a fully closed configuration, and a range of configurations therebetween; (c) a filamentary member attached to the anchoring mechanism for controlling the configuration of the anchoring mechanism; and (d) a controller located at or near the proximal end of the tube for controlling the filamentary member. The improvement comprises an indicator in the controller for visually indicating the anchoring mechanism configuration; a locking mechanism for locking the anchoring mechanism in the fully closed configuration; or a combination of the visual indicator and the locking mechanism.

It is to be understood that both the foregoing general description and the following detailed description are exemplary, but not restrictive, of the invention.

BRIEF DESCRIPTION OF THE DRAWING

The invention is best understood from the following detailed description when read in connection with the accompanying drawing, in which.

DETAILED DESCRIPTION OF THE INVENTION

The invention will next be illustrated with reference to the figures wherein the same numbers indicate similar elements in all figures. Such figures are intended to be illustrative rather than limiting and are included herewith to facilitate the explanation of the apparatus of the present invention.

Figure 2A:
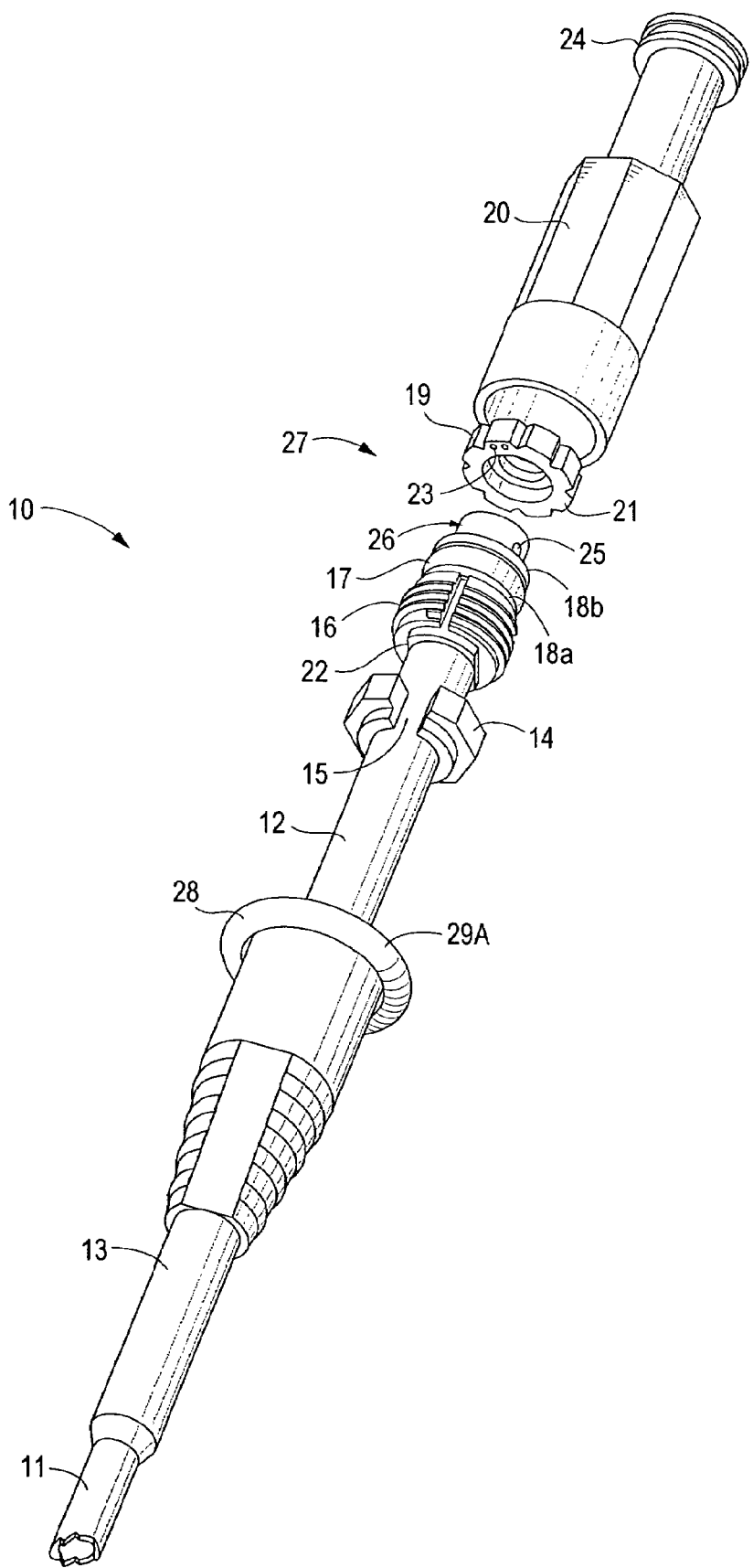
FIG. 2A is a partially exploded, perspective illustration of a controller of the prior art.
Figure 2B:
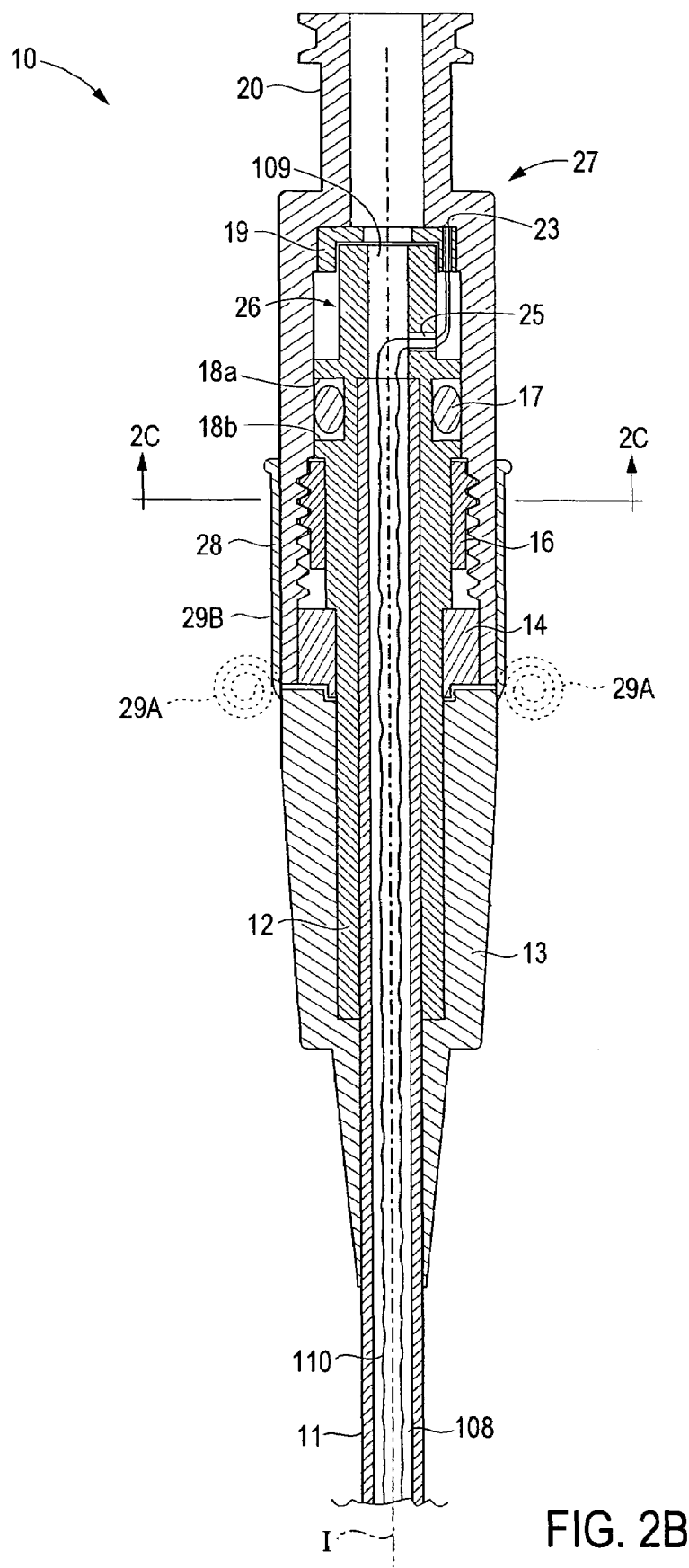
FIG. 2B is a longitudinal section illustration of a portion of the controller cut along line 2B-2B of FIG. 1.
Figure 2C:
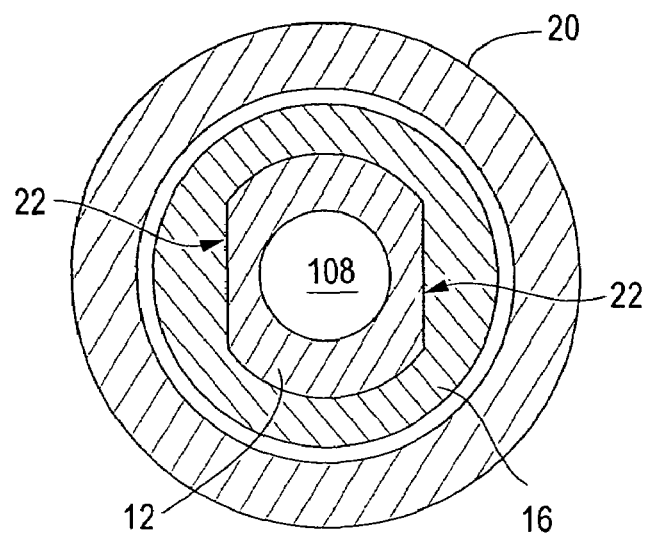
FIG. 2C is a cross-sectional illustration of a portion of the controller cut along line 2C-2C of FIG. 2B.
Figure 3A:
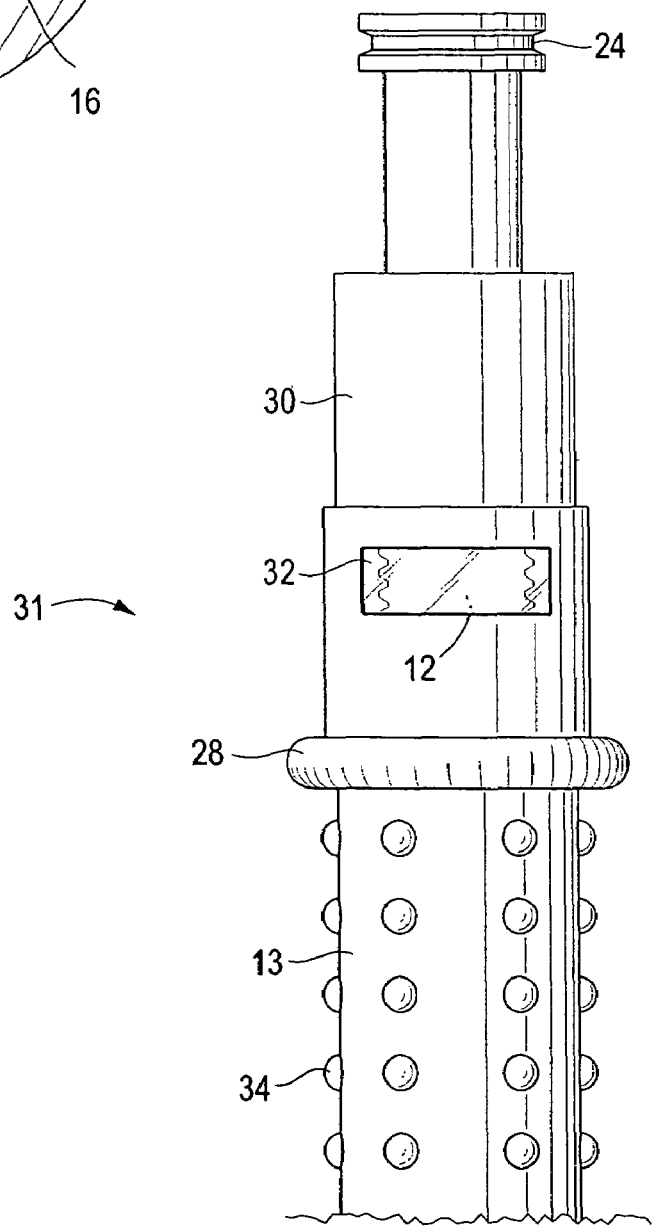
FIG. 3A is a plan view of an exemplary visual indicator embodiment of the invention with the anchoring mechanism in an open position.
Figure 3B:
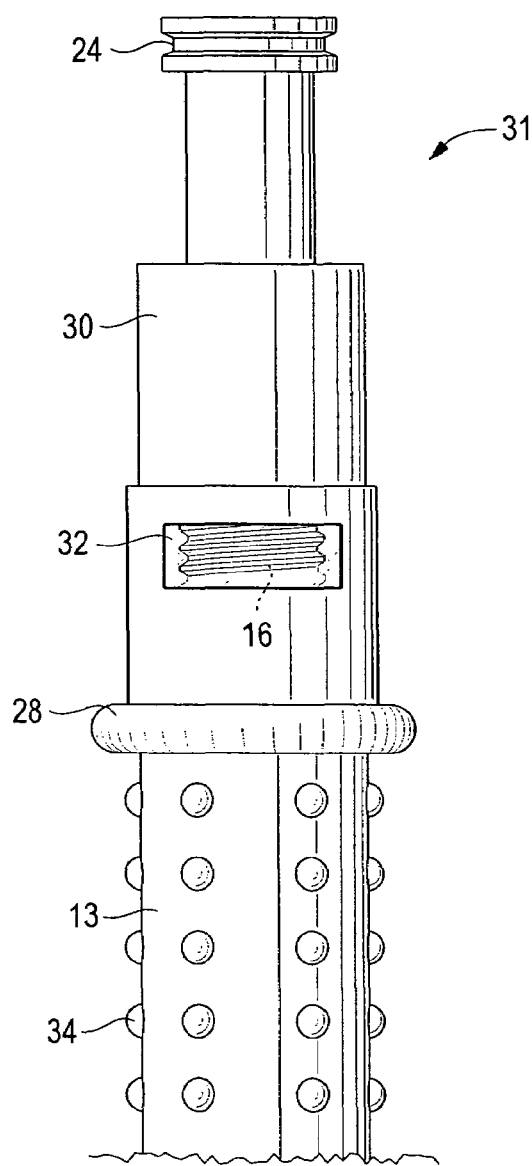
FIG. 3B is a plan view of the embodiment shown in FIG. 3A with the anchoring mechanism in a closed position.
Figure 3C:
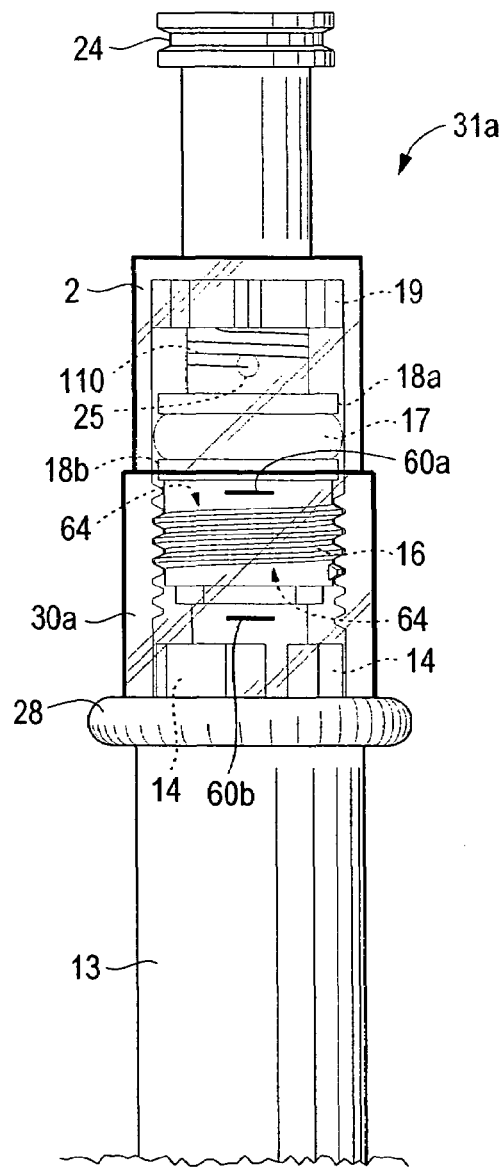
FIG. 3C is a plan view of an exemplary controller embodiment having a transparent hub.
Figure 4:
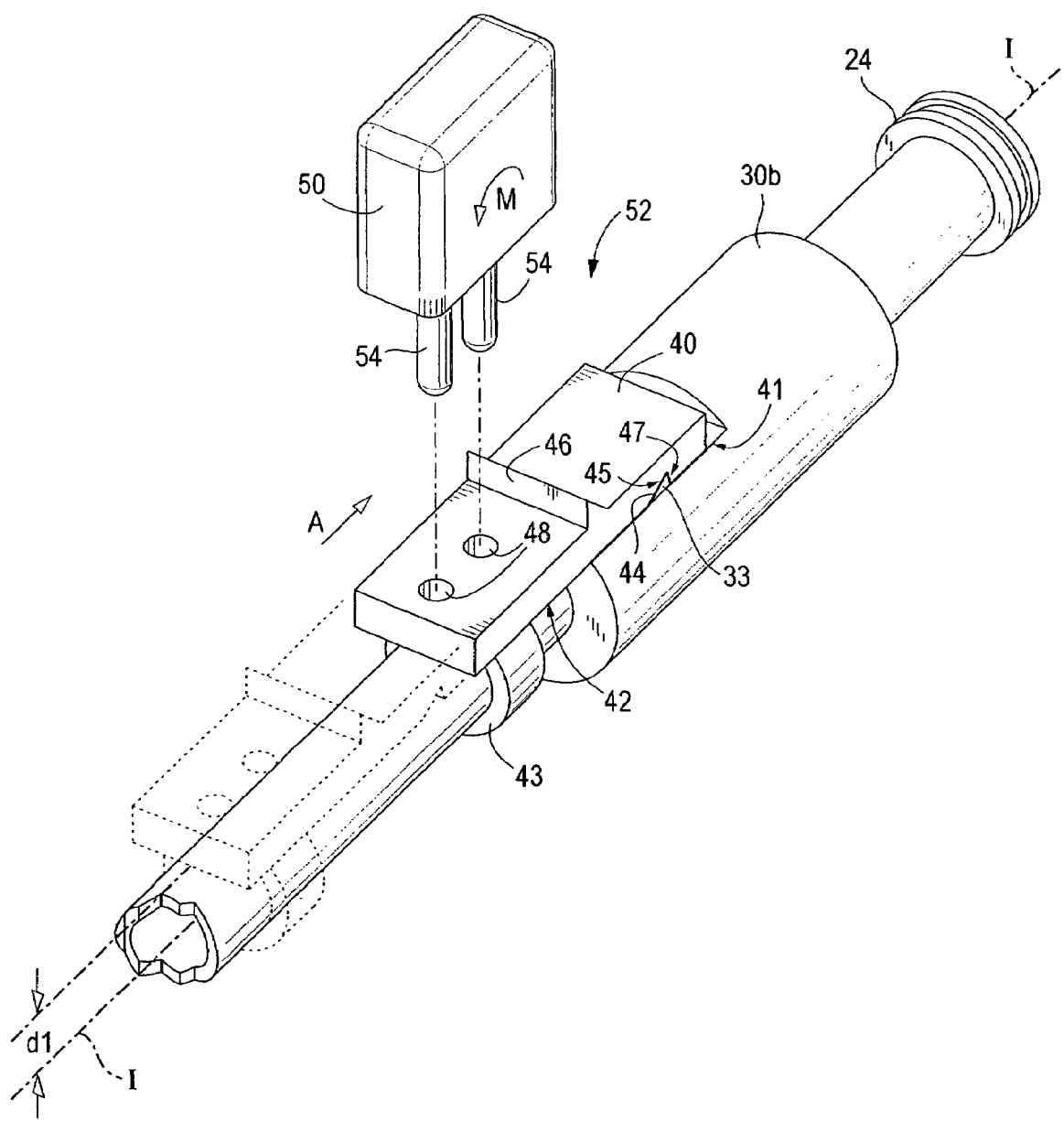
FIG. 4 is a perspective view of an exemplary safety-lock embodiment of the present invention showing the slide in the locked position with solid lines and in the unlocked position with dashed lines.

FIGS. 3A-4 depict embodiments of various aspects of the present invention. FIGS. 3A and 3B show the hub section and strain relief of an exemplary catheter of the invention. In the embodiment described herein, the remaining components may be similar to those shown in FIGS. 1 through 2C. The novel features of this invention are not limited, however, to that or any particular embodiment. Controller 31 comprises a hub section 30 having a window 32 through which the threaded washer 16 is visible when the pigtail 100 shown is in the closed configuration shown in FIG. 1. Thus, as hub 30 is rotated, threaded washer 16 moves axially in a distal direction until it shows through window 32 as shown in FIG. 3B. When the washer is visible, the practitioner knows that the pigtail is in the closed configuration. For ease of viewing, the threaded washer 16 may comprise a red color or other highly visible color to clearly indicate closure. In the alternative, the underlying spindle 12 may be red, and the threaded washer 16 green so that the visual indicator shows red when not closed and green when closed. The invention is not limited, however, to any particular color scheme.

Although shown only with a window 32 in FIGS. 3A and 3B, the entire hub may be transparent, such as hub 30a, shown in FIG. 3C, so that the practitioner may view the position of threaded washer 16. For transparent hub applications, indicia such as lines 60a and 60b, for example, may be marked on the hub such that alignment with the proximal edge 62 of washer 16 with line 60a indicia indicates closure of the pigtail. Similarly, alignment of distal edge 64 of washer 16 with distal line 60b indicates that the pigtail is open. Lines 60a and 60b may be printed, raised, notched, or some combination thereof, such as a line comprising a notch with color therein or a raised surface with a color thereon.

Thus, as shown in FIG. 3C, as the suture 110 is wound about the "reel" comprising outer surface 26 of proximal end 27 of spindle 12 to take up the slack at the distal end, threaded washer 16 moves toward line 60a and can be stopped by the practitioner when edge 62 aligns with line 60a. Thus, for a line of products including different embodiments with different suture amounts to be wound, standard inside components can be used, with different hubs having different locations for line 60a depending on the suture amount. A single embodiment having lines corresponding to all of the different embodiments may also be used, although not preferred because of the risk of confusion of lines by the practitioner.

The transparent window 32 or transparent hub 30a may comprise any clear material known in the art, such as glass or a plastic resin, such as for example, polycarbonate, polystyrene, acrylonitrile butadiene styrene (ABS) or acrylic. The window or hub is not limited to any particular materials of construction, however, and in the window embodiment, may in fact comprise an open cut-out without any transparent covering material for the cutout. The window may also have any shape and may comprise any portion of hub 30 that is transparent, having any geometry. Although strain relief 13 is shown in FIGS. 3A and 3B having a plurality of bumps 34 that are desirable for providing a grip for the user, and in FIG. 3C as being smooth, the invention is not limited, to any particular design of the strain relief.

Figure 1:
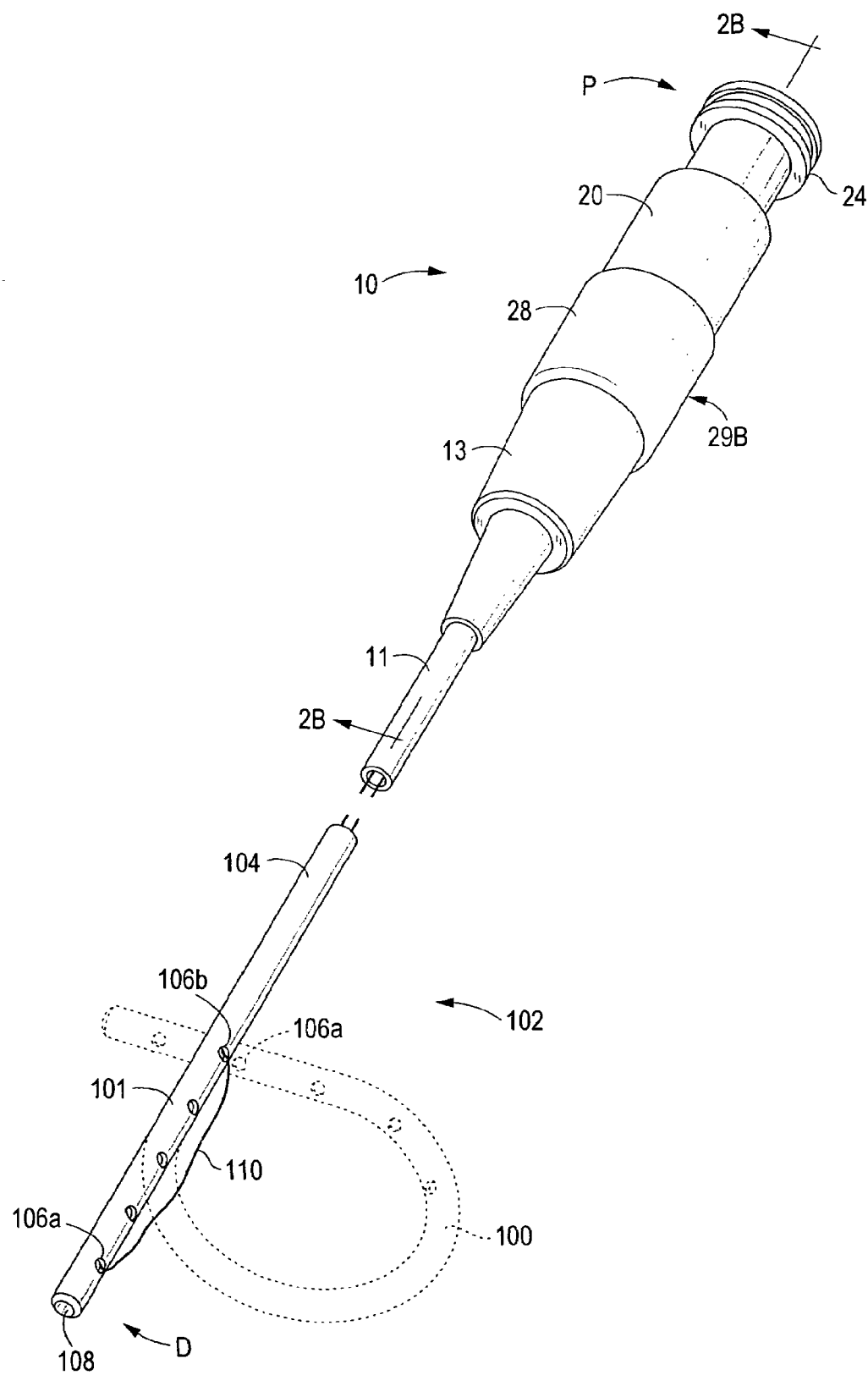
FIG. 1 is a perspective illustration of a catheter having a pigtail anchoring mechanism of the prior art.

Thus the components shown in FIGS. 3A and 3B, combined with FIGS. 1-2C together illustrate one embodiment relating to one aspect of the invention. This embodiment comprises a drainage catheter comprising a tube 11 having an axis I, a distal end D for deployment in a patient, and a proximal end P for remaining outside of the patient. Distal end D of tube 11 comprises a pigtail 100, or any other anchoring mechanism known in the art, having a fully open configuration 100, a fully closed configuration 102, and a range of configurations therebetween. Suture 110, or any other filamentary member known in the art, is attached to pigtail 100 (or other anchoring mechanism) for controlling its configuration. Controller 31, located at or near proximal end P of tube 11 for controlling suture 110 (or other filamentary member), comprises an indicator for visually indicating the anchoring mechanism configuration, such as window 32 through which threaded washer 16 is visible.

The visual indicator is particularly useful for the type of drainage catheter shown in FIGS. 2A-2C, but is not limited thereto. In the embodiment shown in FIGS. 2A and 2B, controller 31 comprises winding washer 18 to which the proximal end of suture 110 is attached. Winding washer 18 is engageable by hub 30 for rotation about axis I to helically wind the suture about the proximal end of the spindle, which acts as a reel on which to wind the suture.

Although in an exemplary embodiment herein where the controller comprises hub 30 that is coaxial with tube 12 and rotatable about axis I and the visual indicator comprises window 32 through which threaded screw 16 is visible when the pigtail 100 is closed, the invention may encompass any catheter design with any type of controller having any relationship to tube 12. The visual indicator is not limited only to a window, but may comprise any type of indicator known in the art.

Although described herein where the visual indicator indicates when the anchoring mechanism is in the fully closed configuration, the visual indicator may also or instead show when the anchoring mechanism is in the fully open configuration. In one embodiment, the visual indicator may indicate the configuration across a range of configurations including and between the fully open and fully closed configurations, such as in an embodiment wherein the entire hub comprises transparent materials and lines or other indicia show the status of the anchoring mechanism across the range of configurations.

Referring now to FIG. 4, there is shown a catheter embodiment having an exemplary locking mechanism 52. Locking mechanism 52 locks anchoring mechanism 100 in the fully closed configuration and prevents unintentional opening when slide 40 is moved into a predetermined position P. As shown in FIG. 4, hub 30b comprises a flattened region 41 adapted to interface with slide 40 to prevent rotation of the hub when slide 40 is in the proximal position (shown with solid lines). Slide 40 is axially slidable between the proximal position and a distal position (shown in dashed lines), but does not rotate about axis I. The non-rotation may be accomplished by providing a non-round cross section in spindle 112, as shown in FIG. 2B and mating non-round cross section on slide washer 43. Slide 40 also comprises ridge 46 for facilitating engagement by the user in the direction of arrow A to lock slide 40 onto hub 30.

Substantially flat radially inward surface 42 is radially spaced a distance $d_1$ from axis I sufficient to engage flattened region 41 of hub 30b when slide 40 is in the proximal position. Although shown in an exemplary embodiment wherein two substantially flat surfaces engage one another, other embodiments may be provided in which the slidable locking mechanism comprises a male member that engages a female member in the hub, or vice versa. Although one exemplary embodiment may comprise both a locking mechanism and a visual indicator, embodiments having one or the other are also within the scope of the invention.

Substantially flat surface 42 of slide 40 further comprises a first surface formation, namely indentation 44, adapted to interlock with a second surface formation in hub 30b, namely protrusion 33, for preventing axial movement of slide 40 when the protrusion and the indent are interlocked. Although shown with a concave indentation 44 on slide surface 42 and a convex protrusion 33 on hub 30b, the hub may have the indentation and the slide may have the protrusion. In the embodiment shown in FIG. 4 with slide 40 engaging hub 30b with protrusion 44 interlocked inside indentation 33, the amount of axial force exerted in the direction opposite arrow A to disengage slide 40 from hub 30b is preferably greater than can be readily exerted by a user without a specialized tool. For example, the design of the indentation 33, protrusion 44, and the angle and size of ridge 46 may be such that a force may be necessary to disengage the protrusion from the indentation beyond what a patient can easily exert with his or her fingers against ridge 46 without his or her fingers sliding off the ridge. In one embodiment, for example, a disengagement force in a range of 10-40 pounds, more preferably about 25 pounds, may be desirable, but the disengagement force may be any amount of force deemed adequate for the conditions of use. Thus, locking mechanism 52 is preferably not unlockable without the use of a specialized tool, such as key 50.

The shape and size of indentation 33, protrusion 44, and ridge 46 may be any geometry found to provide desired properties, and is well within the skill in the art to provide. In some embodiments, it may be particularly desirable for the engagement force to be less than the disengagement force. Thus, for example, as shown in FIG. 4, where protrusion 33 and indentation 44 have a triangular cross-section, the slope of distal side 45 of the protrusion is less than the slope of the proximal side 47 of the protrusion so that the force required to move slide in direction A to engage protrusion 33 in indentation 44 is less than required to move the slide in the opposite direction to disengage the protrusion and indentation. In other embodiments, it may be desired for the forces to be equal, and equal slopes may be provided on the distal and proximal sides. The cross-sectional geometry of indentation 44 and protrusion 33 are not limited to triangular geometries, however, and any geometry suitable to provide properties desired for a particular application may be provided.

Key 50 comprises a pair of posts 54 that fit inside respective openings 48 of slide 40. The key provides leverage for a user to apply both a greater force opposite arrow A than can be readily negotiated on ridge 46, but also apply a moment M to help lift the indentation 33 away from protrusion 44, thereby decreasing the amount of axial force necessary to be exerted to disengage the indentation and protrusion. Considering slide 40 as a lever with slide washer 43 as a fulcrum, the location of the slide washer near the proximal end of the slide 40 leaves little room to apply any downward force to gain any leverage to lift indentation 33. Thus, the ability to lift indentation 33 greatly enhanced by the ability to use key 50.

Thus, one aspect of the invention is a method for deploying a drainage catheter having an anchoring mechanism such as pigtail 100 shown in FIG. 1 and a visual indicator such as the window 32 and threaded screw 16 shown in FIGS. 3A and 3B, as described herein. Such a method comprises inserting catheter into a patient with the anchoring mechanism in the fully open configuration; and manipulating the controller until the indicator indicates that the anchoring mechanism is in the fully closed configuration. Where such a catheter further comprises a locking mechanism such as slide 40, the method may further comprise engaging the slide, such as by moving it into proximal position, to lock anchoring mechanism 100 in the fully closed configuration and prevent unintentional opening thereof. Where the locking mechanism further comprises a mechanism, such as mechanism 52, for preventing unlocking thereof without a specialized tool, such as key 50, the method further comprises unlocking the locking mechanism using the specialized tool, manipulating the anchoring mechanism into the open configuration; and removing the drainage catheter from the patient. To advantageously prevent unauthorized tampering by patients, only doctors and/or nurses may be provided with keys 50.

Furthermore, although illustrated and described herein with reference to certain specific embodiments, the present invention is nevertheless not intended to be limited to the details shown. Rather, various modifications may be made in the details within the scope and range of equivalents of the claims and without departing from the spirit of the invention.

What is claimed:

1. A catheter comprising:
    a tube having an axis, a distal end for deployment in a patient, and a proximal end for remaining outside of the patient;
    an anchoring mechanism at the distal end of the tube having a fully open configuration, a fully closed configuration, and a range of configurations therebetween;
    a filamentary member attached to the anchoring mechanism for controlling the configuration of the anchoring mechanism; and
    a controller located at or near the proximal end of the tube for controlling the filamentary member, the controller comprising a locking mechanism for locking the anchoring mechanism in the fully closed configuration and a first member comprising a first region adapted to interface with the locking mechanism to prevent rotation of the first member when the locking mechanism is in a locked configuration.

2. The catheter of claim 1, wherein the locking mechanism comprises a slide that is not rotatable on the axis relative to the tube, but is movable axially relative to the tube between a proximal position and a distal position, and that has a substantially flat radially inward surface that is radially spaced a first radial distance from the axis, the first region comprising a flattened region of the first member adapted to be engaged by the substantially flat surface of the slide when the slide is in the proximal position.

3. The catheter of claim 2, wherein the substantially flat surface comprises a first surface formation adapted to engage a second surface formation in the first member and requires a threshold axial force to unlock the slide when the first surface formation and the second surface formation are interlocked.

4. The catheter of claim 3, wherein the threshold axial force is in a range of 10 to 40 pounds.

5. The catheter of claim 3, wherein the threshold axial force is about 25 pounds.

6. The catheter of claim 3, wherein the first surface formation comprises a protrusion and the second surface formation comprises an indentation, or vice versa.

7. The catheter of claim 3, wherein the first surface formation and the second surface formation have a triangular cross section having a distal slope and a proximal slope.

8. The catheter of claim 7, wherein the distal slope is less than the proximal slope.

9. The catheter of claim 7, wherein the distal slope is equal to the proximal slope.

10. The catheter of claim 3, wherein a first axial force required to interlock the first surface formation with the second surface formations is less than a second axial force required to disengage the interlocked first surface formation and second surface formation.

11. The catheter of claim 3, wherein the slide further comprises a specialized tool for disengaging the interlocked first surface formation and second surface formation.

12. The catheter of claim 11, wherein the specialized tool comprises a key.

13. The catheter of claim 12, wherein the slide has a proximal end and a distal end, the slide is attached to a slide washer that engages the tube adjacent a distal axial end of the slide, and the key comprises means for exerting a moment to lift the proximal end of the slide off of the flattened region of the first member while applying a distal axial force.

14. The catheter of claim 13, wherein the slide comprises one or more openings and the key comprises one or more posts for insertion in the one or more openings, or vice versa.

15. The catheter of claim 14, wherein the key comprises a flat underside and the slide comprises a flat top surface, the flat underside adapted to contact the flat top surface when the posts and openings are engaged.

16. The catheter of claim 1, wherein the locking mechanism further comprises a specialized tool for unlocking the mechanism.

17. The catheter of claim 1, wherein the anchoring mechanism comprises a pigtail.

18. A catheter comprising:
a tube having an axis, a distal end for deployment in a patient, a proximal end for remaining outside of the patient, and having a first lumen therethrough;
an anchoring mechanism at the distal end of the tube having a fully open configuration, a fully closed configuration, and a range of configurations therebetween;
a filamentary member attached to the anchoring mechanism for controlling the configuration of the anchoring mechanism;
a controller located at or near the proximal end of the tube for controlling the filamentary member, the controller comprising
a spindle coaxially mounted on the tube and having a proximal reel portion comprising an outer surface having a winding diameter, a second lumen extending proximally from the first lumen, and a radial port connecting the outer surface with the second lumen,
a hub coaxial with the tube and the spindle, rotatable about the axis, and having internal threads, the hub having a window therein,
an axially translatable threaded washer coaxial with the spindle, non-rotatable relative to the spindle, having external threads for mating with the internal threads of the hub, and
a winding washer axially rotatable about the spindle to which a proximal end of the filamentary member is attached; and
a locking mechanism comprising a slide that is not rotatable on the axis relative to the tube, but is movable axially relative to the tube between a locked position and an unlocked position, and that has a substantially flat radially inward surface that is radially spaced a first radial distance from the axis
wherein the filamentary member extends through the first lumen into the second lumen and out through the radial port to the winding washer such that twisting the hub about the axis rotates the winding washer and helically winds the filamentary member about the reel portion outer surface while also axially translating the threaded washer so that the threaded washer is visible within the hub window for visually indicating when the anchoring mechanism is in the closed configuration.

19. The catheter of claim 18, wherein the controller further comprises a first member having a first region comprising a flattened region adapted to be engaged by the substantially flat surface of the slide when the slide is in the locked position.

20. The catheter of claim 19, wherein the substantially flat radially inward surface comprises a protrusion and the substantially flat region of the hub comprises an indentation, or vice versa, for engaging one another in the locked position.

21. The catheter of claim 20, further comprising using a specialized tool to disengage the slide from the locked position.

22. A catheter comprising:
a tube having an axis, a distal end for deployment in a patient, and a proximal end for remaining outside of the patient;
an anchoring mechanism at the distal end of the tube having a fully open configuration, a fully closed configuration, and a range of configurations therebetween;
a filamentary member attached to the anchoring mechanism for controlling the configuration of the anchoring mechanism; and
a controller located at or near the proximal end of the tube for controlling the filamentary member, the controller comprising:
a spindle coaxially mounted on the tube and having a proximal reel portion comprising an outer surface having the winding diameter, a second lumen extending proximally from the first lumen, and a radial port connecting the outer surface with the second lumen;

a hub coaxial with the tube and the spindle, rotatable about the axis, and having internal threads, the hub having a substantially flat region;

an axially translatable threaded washer coaxial with the spindle, non-rotatable relative to the spindle, having external threads for mating with the internal threads of the hub;

a winding washer axially rotatable about the spindle to which a proximal end of the filamentary member is attached; and a slide, non-rotatable about the axis relative to the tube, movable axially relative to the tube between a proximal position and a distal position, and having a substantially flat radially inward surface that is radially spaced a first radial distance from the axis and adapted to engage the substantially flat region of the hub when the slide is in the proximal position to lock the hub in a fixed rotational position;

wherein the filamentary member extends through the first lumen into the second lumen and out through the radial port to the winding washer such that twisting the hub about the axis rotates the winding washer and helically winds the filamentary member about the reel portion outer surface while also axially translating the threaded washer.

23. The catheter of claim 22, wherein the substantially flat surface comprises a first surface formation adapted to engage a second surface formation in the first member and requires a threshold axial force to unlock the slide when the first surface formation and the second surface formation are interlocked.

24. The catheter of claim 22, further comprising using a specialized tool to disengage the slide from the locked position.

25. In a catheter comprising (a) a tube having an axis, a distal end for deployment in a patient, and a proximal end for remaining outside of the patient; (b) an anchoring mechanism at the distal end of the tube having a fully open configuration, a fully closed configuration, and a range of configurations therebetween; (c) a filamentary member attached to the anchoring mechanism for controlling the configuration of the anchoring mechanism; and (d) a controller located at or near the proximal end of the tube for controlling the filamentary member, the improvement comprising the controller comprising:

(e) a visual indicator for indicating the anchoring mechanism configuration; and (f) a locking mechanism for locking the anchoring mechanism in the fully closed configuration.

* * * * *